US008439868B2

(12) United States Patent  
Speck et al.

(10) Patent No.: US 8,439,868 B2  
(45) Date of Patent: May 14, 2013

(54) MEDICAL DEVICE FOR DISPERSING MEDICAMENTS

(75) Inventors: Ulrich Speck, Berlin (DE); Bruno Scheller, Saarbrücken (DE)

(73) Assignee: Bayer Pharma AG, Berlin (DE)

( * ) Notice: Subject to any disclaimer, the term of this patent is extended or adjusted under 35 U.S.C. 154(b) by 120 days.

(21) Appl. No.: 12/782,989

(22) Filed: May 19, 2010

(65) Prior Publication Data

US 2010/0228228 A1 Sep. 9, 2010

Related U.S. Application Data

(62) Division of application No. 10/528,577, filed as application No. PCT/DE03/02871 on Aug. 26, 2003, now Pat. No. 8,257,305.

(30) Foreign Application Priority Data

Sep. 20, 2002 (DE) .................................. 102 14 847

(51) Int. Cl.  
*A61M 29/00* (2006.01)

(52) U.S. Cl.  
USPC .................................. 604/103.02; 623/1.11

(58) Field of Classification Search ............. 604/103.02; 623/1.11  
See application file for complete search history.

(56) References Cited

U.S. PATENT DOCUMENTS

| 4,101,984 A | 7/1978 | MacGregor |
| 4,217,894 A | 8/1980 | Franetzki et al. |
| 4,247,352 A | 1/1981 | Stupp et al. |
| 4,305,926 A | 12/1981 | Everse et al. |
| 4,343,788 A | 8/1982 | Mustacich et al. |
| 4,364,921 A | 12/1982 | Speck et al. |
| 4,476,590 A | 10/1984 | Scales et al. |
| 4,479,795 A | 10/1984 | Mustacich et al. |
| 4,502,159 A | 3/1985 | Woodroof et al. |
| 4,532,315 A | 7/1985 | Letoffe et al. |
| 4,573,476 A | 3/1986 | Ruiz et al. |
| 4,677,143 A | 6/1987 | Laurin et al. |
| 4,769,013 A | 9/1988 | Lorenz et al. |
| 4,776,337 A | 10/1988 | Palmaz et al. |
| 4,793,825 A | 12/1988 | Benjamin et al. |
| 4,872,867 A | 10/1989 | Joh |
| 4,879,135 A | 11/1989 | Greco et al. |
| 4,886,062 A | 12/1989 | Wildor et al. |
| 4,909,799 A | 3/1990 | Thulesius et al. |
| 4,917,686 A | 4/1990 | Bayston et al. |
| 4,925,668 A | 5/1990 | Khan et al. |
| 4,950,256 A | 8/1990 | Luther et al. |
| 4,994,047 A | 2/1991 | Walker et al. |
| 4,997,643 A | 3/1991 | Partain et al. |
| 5,004,461 A | 4/1991 | Wilson et al. |
| 5,019,096 A | 5/1991 | Fox, Jr. et al. |
| 5,019,393 A | 5/1991 | Ito et al. |
| 5,019,601 A | 5/1991 | Allen |
| 5,051,257 A | 9/1991 | Pietronigro |
| 5,053,048 A | 10/1991 | Pinchuk |
| 5,059,166 A | 10/1991 | Fischell et al. |
| 5,067,491 A | 11/1991 | Taylor et al. |
| 5,098,977 A | 3/1992 | Frautschi et al. |
| 5,102,402 A * | 4/1992 | Dror et al. ...................... 604/265 |
| 5,108,424 A | 4/1992 | Hoffman et al. |
| 5,112,457 A | 5/1992 | Marchant |
| 5,135,516 A | 8/1992 | Sahatjian et al. |
| 5,157,049 A | 10/1992 | Haugwitz et al. |
| 5,163,952 A | 11/1992 | Froix |
| 5,165,952 A | 11/1992 | Solomon et al. |
| 5,171,217 A | 12/1992 | March et al. |
| 5,176,626 A | 1/1993 | Soehendra et al. |
| 5,182,317 A | 1/1993 | Winters et al. |
| 5,197,977 A | 3/1993 | Hoffman et al. |
| 5,217,493 A | 6/1993 | Raad et al. |
| 5,222,971 A | 6/1993 | Willard et al. |
| 5,229,172 A | 7/1993 | Cahalan et al. |
| 5,232,685 A | 8/1993 | Speck et al. |
| 5,234,456 A | 8/1993 | Silvestrini |
| 5,244,654 A | 9/1993 | Narayanan |
| 5,282,823 A | 2/1994 | Schwartz et al. |
| 5,288,711 A | 2/1994 | Mitchell et al. |
| 5,298,255 A | 3/1994 | Sawamoto et al. |
| 5,304,121 A | 4/1994 | Sahatjian |

(Continued)

FOREIGN PATENT DOCUMENTS

| CA | 2 132 936 AA | 3/1995 |
| CA | 2 207 025 | 6/1996 |

(Continued)

OTHER PUBLICATIONS

"Water soluble paclitaxel prodrugs," Espacenet, Publication Date: Jun. 27, 2000; English Abstract of JP-2000 507930.  
Buaayu KK, "Balloon catheter for intravascular dosing," Patent Abstracts of Japan, Publication Date: Mar. 8, 1994; English Abstract of JP-06 063145.  
Magna International Toronto, "Process for producing a plastic cladding component and cladding component produced especially by said process," Espacenet, Publication Date: Aug. 22, 1996; English Abstract of WO-96 25282.  
Terumo Corp., "Medicine dosing catheter," Patent Abstracts of Japan, Publication Date: Dec. 19, 1995; English Abstract of JP-07 328124.  
Thomson Innovation, Patent Record View, Publication Date: Jan. 19, 1995; English abstract of JP-7 500585.  
Thomson Innovation, Patent Record View, Publication Date: Sep. 22, 1998; English abstract of JP-10 509691.  
Herberts & Co GMBH, "Liquid mixtures of photo-initiators, process for their production and their use," Espacenet, Publication Date: Nov. 26, 1992; English Abstract of WO-92 20718.

(Continued)

*Primary Examiner* — Manuel Mendez  
(74) *Attorney, Agent, or Firm* — Millen, White, Zelano & Branigan, P.C.

(57) ABSTRACT

The present disclosure relates to balloon catheter medical devices. Some balloon catheter medical devices may include a balloon surface having paclitaxel embedded in a low-molecular weight matrix substance adhered thereto and dried. The dried paclitaxel may be immediately releasable after coming into contact with tissue. Other balloon catheter medical devices may include a balloon surface having a lipophilic proliferation inhibitor, an inflammation inhibitor, or an antioxidant adhered thereto.

20 Claims, No Drawings

U.S. PATENT DOCUMENTS

| | | | |
|---|---|---|---|
| 5,306,286 A | 4/1994 | Stack et al. |
| 5,314,688 A | 5/1994 | Kauffman et al. |
| 5,320,634 A | 6/1994 | Vigil et al. |
| 5,342,348 A | 8/1994 | Kaplan |
| 5,344,411 A | 9/1994 | Domb et al. |
| 5,344,444 A | 9/1994 | Glastra |
| 5,345,933 A | 9/1994 | Peterson et al. |
| 5,348,873 A | 9/1994 | Matsuda et al. |
| 5,356,433 A | 10/1994 | Rowland et al. |
| 5,370,614 A | 12/1994 | Amundson et al. |
| 5,380,299 A | 1/1995 | Fearmot et al. |
| 5,383,927 A | 1/1995 | De Golcoechea et al. |
| 5,383,928 A | 1/1995 | Scott et al. |
| 5,419,760 A | 5/1995 | Narciso, Jr. |
| 5,443,458 A | 8/1995 | Eury |
| 5,447,724 A | 9/1995 | Helmus et al. |
| 5,449,382 A | 9/1995 | Dayton et al. |
| 5,454,886 A | 10/1995 | Burrell et al. |
| 5,455,040 A | 10/1995 | Marchant |
| 5,456,663 A | 10/1995 | Lemelson |
| 5,457,113 A | 10/1995 | Cillinan et al. |
| 5,464,450 A | 11/1995 | Buscemi et al. |
| 5,464,650 A | 11/1995 | Berg et al. |
| 5,500,013 A | 3/1996 | Buscemi et al. |
| 5,504,102 A | 4/1996 | Agharkar et al. |
| 5,510,330 A | 4/1996 | Martin et al. |
| 5,531,716 A | 7/1996 | Luzio et al. |
| 5,534,288 A | 7/1996 | Gruskin et al. |
| 5,554,181 A | 9/1996 | Das |
| 5,554,182 A | 9/1996 | Dinh et al. |
| 5,559,448 A | 9/1996 | Koenig et al. |
| 5,567,495 A | 10/1996 | Modak et al. |
| 5,569,463 A | 10/1996 | Helmus et al. |
| 5,571,086 A | 11/1996 | Kaplan et al. |
| 5,578,075 A | 11/1996 | Dayton |
| 5,605,696 A | 2/1997 | Eury et al. |
| 5,607,463 A | 3/1997 | Schwartz et al. |
| 5,607,475 A | 3/1997 | Cahalan et al. |
| 5,609,629 A | 3/1997 | Fearmot et al. |
| 5,624,411 A | 4/1997 | Tuch |
| 5,626,562 A | 5/1997 | Castro |
| 5,629,008 A | 5/1997 | Lee |
| 5,629,881 A | 5/1997 | Leeb et al. |
| 5,643,580 A | 7/1997 | Subramaniam et al. |
| 5,649,977 A | 7/1997 | Campbell et al. |
| 5,674,192 A | 10/1997 | Sahatjian |
| 5,679,400 A | 10/1997 | Tuch |
| 5,681,846 A | 10/1997 | Trissel |
| 5,693,014 A | 12/1997 | Abele et al. |
| 5,697,967 A | 12/1997 | Dinh et al. |
| 5,716,981 A | 2/1998 | Hunter et al. |
| 5,733,327 A | 3/1998 | Igaki et al. |
| 5,762,638 A | 6/1998 | Shikani et al. |
| 5,766,158 A | 6/1998 | Opolski |
| 5,770,198 A | 6/1998 | Coller et al. |
| 5,772,640 A | 6/1998 | Modak et al. |
| 5,789,018 A | 8/1998 | Engelson et al. |
| 5,792,158 A | 8/1998 | Lary |
| 5,814,301 A | 9/1998 | Klopp |
| 5,820,607 A | 10/1998 | Tcholakian et al. |
| 5,824,049 A | 10/1998 | Ragheb et al. |
| 5,827,289 A | 10/1998 | Reiley |
| 5,837,008 A | 11/1998 | Berg et al. |
| 5,863,745 A | 1/1999 | Fitzgerald et al. |
| 5,873,904 A | 2/1999 | Ragheb et al. |
| 5,886,026 A | 3/1999 | Hunter et al. |
| 5,893,867 A | 4/1999 | Bagaisan et al. |
| 5,902,283 A | 5/1999 | Darouiche et al. |
| 5,916,596 A * | 6/1999 | Desai et al. ............ 424/489 |
| 5,921,952 A | 7/1999 | Desmond et al. |
| 5,922,754 A | 7/1999 | Burchett et al. |
| 5,954,706 A | 9/1999 | Sahatjian |
| 5,977,163 A | 11/1999 | Li et al. |
| 5,980,972 A | 11/1999 | Ding |
| 5,981,568 A | 11/1999 | Kunz et al. |
| 5,997,162 A | 12/1999 | English et al. |
| 6,010,480 A | 1/2000 | Abele et al. |
| 6,013,092 A | 1/2000 | Dehdashtian et al. |
| 6,017,948 A | 1/2000 | Rubinfeld et al. |
| 6,039,721 A | 3/2000 | Johnson et al. |
| 6,071,285 A | 6/2000 | Lashinski et al. |
| 6,096,070 A | 8/2000 | Ragheb et al. |
| 6,123,923 A | 9/2000 | Unger et al. |
| 6,146,358 A | 11/2000 | Rowe et al. |
| 6,171,232 B1 | 1/2001 | Papandreau et al. |
| 6,177,061 B1 * | 1/2001 | Klaveness et al. ............ 424/9.51 |
| 6,203,487 B1 | 3/2001 | Consigny et al. |
| 6,203,551 B1 | 3/2001 | Wu et al. |
| 6,207,133 B1 | 3/2001 | Reszka et al. |
| 6,214,333 B1 | 4/2001 | Zoldhelyi et al. |
| 6,221,467 B1 | 4/2001 | Nazarova et al. |
| 6,231,615 B1 | 5/2001 | Preissman et al. |
| 6,240,616 B1 | 6/2001 | Yan |
| 6,248,100 B1 | 6/2001 | de Toledo et al. |
| 6,258,108 B1 | 7/2001 | Lary |
| 6,264,624 B1 | 7/2001 | Desmond et al. |
| 6,273,908 B1 | 8/2001 | Ndondo-Lay |
| 6,273,913 B1 | 8/2001 | Wright et al. |
| 6,287,285 B1 | 9/2001 | Michal et al. |
| 6,299,604 B1 | 10/2001 | Ragheb et al. |
| 6,306,151 B1 | 10/2001 | Lary et al. |
| 6,306,166 B1 * | 10/2001 | Barry et al. ................ 623/1.46 |
| 6,335,029 B1 | 1/2002 | Kamath et al. |
| 6,339,039 B1 | 1/2002 | Porath et al. |
| 6,355,058 B1 | 3/2002 | Pacetti et al. |
| 6,364,856 B1 | 4/2002 | Ding et al. |
| 6,369,039 B1 | 4/2002 | Palasis et al. |
| 6,369,093 B1 | 4/2002 | Elbe et al. |
| 6,375,931 B2 | 4/2002 | Ostensen |
| 6,400,448 B1 | 6/2002 | Sugawara et al. |
| 6,406,754 B2 | 6/2002 | Chappa et al. |
| 6,419,692 B1 | 7/2002 | Yang et al. |
| 6,479,033 B1 | 11/2002 | Reszka et al. |
| 6,491,619 B1 | 12/2002 | Trauthen et al. |
| 6,491,938 B2 | 12/2002 | Kunz et al. |
| 6,495,579 B1 | 12/2002 | Hunter et al. |
| 6,500,341 B2 | 12/2002 | Wang et al. |
| 6,503,954 B1 | 1/2003 | Bhat et al. |
| 6,515,016 B2 | 2/2003 | Hunter et al. |
| 6,544,223 B1 | 4/2003 | Kokish et al. |
| 6,544,544 B2 | 4/2003 | Hunter et al. |
| 6,562,024 B2 | 5/2003 | de Toledo et al. |
| 6,575,888 B2 | 6/2003 | Zamora et al. |
| 6,585,765 B1 | 7/2003 | Hossainy et al. |
| 6,599,275 B1 | 7/2003 | Fischer et al. |
| 6,599,448 B1 | 7/2003 | Ehrhard et al. |
| 6,599,928 B2 | 7/2003 | Kunz et al. |
| 6,616,591 B1 | 9/2003 | Toeh et al. |
| 6,616,650 B1 | 9/2003 | Rowe |
| 6,635,082 B1 | 10/2003 | Hossainy et al. |
| 6,638,913 B1 | 10/2003 | Amplatz |
| 6,682,545 B1 | 1/2004 | Kester |
| 6,682,546 B2 | 1/2004 | Amplatz |
| 6,695,811 B2 | 2/2004 | Samson et al. |
| 6,706,892 B1 | 3/2004 | Ezrin et al. |
| 6,730,064 B2 | 5/2004 | Ragheb et al. |
| 6,774,278 B1 | 8/2004 | Ragheb et al. |
| 6,867,190 B2 | 3/2005 | Carney et al. |
| 6,918,927 B2 | 7/2005 | Bates et al. |
| 7,060,051 B2 | 6/2006 | Palasis et al. |
| 7,179,251 B2 | 2/2007 | Palasis et al. |
| 7,419,683 B2 | 9/2008 | Szebeni et al. |
| 7,445,792 B2 | 11/2008 | Toner et al. |
| 7,491,234 B2 | 2/2009 | Palasis et al. |
| 7,611,532 B2 | 11/2009 | Bates et al. |
| 7,731,685 B2 | 6/2010 | Ragheb et al. |
| 7,750,041 B2 | 7/2010 | Speck et al. |
| 7,811,622 B2 | 10/2010 | Bates et al. |
| 2001/0014717 A1 | 8/2001 | Hossainy et al. |
| 2001/0034363 A1 | 10/2001 | Li et al. |
| 2001/0037140 A1 | 11/2001 | Gaudoin et al. |
| 2001/0044651 A1 | 11/2001 | Steinke et al. |
| 2002/0013549 A1 | 1/2002 | Zhong et al. |
| 2002/0032414 A1 | 3/2002 | Ragheb et al. |
| 2002/0037358 A1 | 3/2002 | Barry et al. |
| 2002/0098278 A1 | 7/2002 | Bates et al. |
| 2002/0123505 A1 | 9/2002 | Burke et al. |

| | | | | | | |
|---|---|---|---|---|---|---|
| 2002/0193828 | A1 | 12/2002 | Griffin et al. | EP | 1 512 398 | 3/2005 |
| 2003/0007944 | A1 | 1/2003 | O'Halloran et al. | EP | 1 521 603 | 4/2005 |
| 2003/0028243 | A1 | 2/2003 | Bates et al. | EP | 1 536 850 | 6/2005 |
| 2003/0028244 | A1 | 2/2003 | Bates et al. | EP | 1 666 070 | 6/2006 |
| 2003/0036794 | A1 | 2/2003 | Ragheb et al. | EP | 1 666 071 A1 | 6/2006 |
| 2003/0059454 | A1 | 3/2003 | Barry et al. | EP | 1 669 091 | 6/2006 |
| 2003/0100600 | A1 | 5/2003 | Kinsella et al. | EP | 1 669 092 | 6/2006 |
| 2003/0195548 | A1 | 10/2003 | Kester | EP | 1 372 737 B1 | 8/2006 |
| 2004/0068241 | A1 | 4/2004 | Fischer | EP | 1 695 697 | 8/2006 |
| 2004/0073284 | A1* | 4/2004 | Bates et al. ........... 623/1.11 | EP | 1 695 698 | 8/2006 |
| 2004/0115228 | A1 | 6/2004 | Costa et al. | EP | 1 735 042 | 12/2006 |
| 2004/0224003 | A1 | 11/2004 | Schultz | EP | 1 781 209 | 5/2007 |
| 2004/0243225 | A1 | 12/2004 | Ragheb et al. | EP | 2 092 941 | 8/2009 |
| 2005/0042295 | A1 | 2/2005 | Hunter et al. | EP | 2 092 942 | 8/2009 |
| 2005/0063926 | A1 | 3/2005 | Bathina et al. | EP | 2 098 230 | 9/2009 |
| 2005/0101522 | A1 | 5/2005 | Speck et al. | JP | 06 063145 | 3/1994 |
| 2005/0123605 | A1 | 6/2005 | Hunter et al. | JP | 7500585 | 1/1995 |
| 2005/0222677 | A1 | 10/2005 | Bates et al. | JP | 07 328124 | 12/1995 |
| 2005/0250672 | A9 | 11/2005 | Speck et al. | JP | 10 509691 | 9/1998 |
| 2005/0278021 | A1 | 12/2005 | Bates et al. | JP | 10509691 | 9/1998 |
| 2006/0020243 | A1 | 1/2006 | Speck et al. | JP | 11012160 A | 1/1999 |
| 2006/0020331 | A1 | 1/2006 | Bates et al. | JP | 2000 507930 | 6/2000 |
| 2007/0128118 | A1 | 6/2007 | Yu et al. | JP | 2001-508320 | 6/2001 |
| 2008/0010234 | A1 | 1/2008 | Nakagawa et al. | JP | 2002-536058 | 10/2002 |
| 2008/0012034 | A1 | 1/2008 | Thielen et al. | WO | WO 90/13293 | 11/1990 |
| 2008/0102033 | A1 | 5/2008 | Speck et al. | WO | WO-90 13293 | 11/1990 |
| 2008/0102034 | A1 | 5/2008 | Speck et al. | WO | WO 90/13332 | 11/1990 |
| 2008/0118544 | A1 | 5/2008 | Wang et al. | WO | WO-90 13332 | 11/1990 |
| 2008/0175887 | A1 | 7/2008 | Wang et al. | WO | WO-91 12779 | 9/1991 |
| 2008/0255508 | A1 | 10/2008 | Wang et al. | WO | WO 91/12779 | 9/1991 |
| 2008/0255509 | A1 | 10/2008 | Wang et al. | WO | WO 92/11896 | 7/1992 |
| 2008/0255510 | A1 | 10/2008 | Wang et al. | WO | WO-92 11896 | 7/1992 |
| | | | | WO | WO 9211890 | 7/1992 |
| | FOREIGN PATENT DOCUMENTS | | | WO | WO 92/12717 | 8/1992 |
| CA | 2207025 AA | | 6/1996 | WO | WO-92 12717 | 8/1992 |
| CA | 2 218 103 | | 10/1996 | WO | WO 9215282 | 9/1992 |
| CA | 2 345 729 AA | | 4/2000 | WO | WO-92 20718 | 11/1992 |
| CA | 2 345 697 AA | | 5/2000 | WO | WO 92/20718 | 11/1992 |
| CN | 1 224 622 A | | 8/1999 | WO | WO 92/20718 A2 | 11/1992 |
| DE | 69403966 | | 7/1993 | WO | WO 93/06792 | 4/1993 |
| DE | 4225553 | | 5/1994 | WO | WO 93/07875 | 4/1993 |
| DE | 4 334 272 | | 4/1995 | WO | WO-93 07875 | 4/1993 |
| DE | 43 34 272 | | 4/1995 | WO | WO 93/09762 | 5/1993 |
| DE | 4341478 A1 | | 6/1995 | WO | WO-93 09762 | 5/1993 |
| DE | 44 35 652 | | 4/1996 | WO | WO-93 09765 | 5/1993 |
| DE | 4 446 694 | | 6/1996 | WO | WO 93/09765 | 5/1993 |
| DE | 44 46 694 | | 6/1996 | WO | WO-93 11120 | 6/1993 |
| DE | 195 14 104 | | 11/1996 | WO | WO 93/11120 | 6/1993 |
| DE | 69119753 | | 1/1997 | WO | WO 93/11668 | 6/1993 |
| DE | 69 403 966 | | 2/1998 | WO | WO-93 11668 | 6/1993 |
| DE | 19724796 A1 | | 12/1998 | WO | WO 00/50105 A2 | 2/1994 |
| DE | 10115740 | | 10/2002 | WO | WO 94/07484 | 4/1994 |
| DE | 10 244 847 | | 4/2004 | WO | WO-94 07484 | 4/1994 |
| DE | 102 44 847.7 | | 4/2004 | WO | WO-94 07529 | 4/1994 |
| DE | 69925936 | | 7/2005 | WO | WO 94/07529 | 4/1994 |
| DE | 20 122 736 | | 7/2007 | WO | WO-94 16706 | 8/1994 |
| DE | 20 122 736.3 | | 7/2007 | WO | WO 94/16706 | 8/1994 |
| EP | 1 118 325 B1 | | 11/1986 | WO | WO 94/23787 | 10/1994 |
| EP | 0 357 003 | | 3/1990 | WO | WO-94 23787 | 10/1994 |
| EP | 0 470 246 | | 2/1992 | WO | WO 94/23787 A1 | 10/1994 |
| EP | 0 578 998 | | 1/1994 | WO | WO 94/25020 | 11/1994 |
| EP | 0 604 022 | | 6/1994 | WO | WO-94 25020 | 11/1994 |
| EP | 0 623 354 | | 11/1994 | WO | WO 94/26291 | 11/1994 |
| EP | 0 673 114 | | 9/1995 | WO | WO-94 26291 | 11/1994 |
| EP | 0 681 475 | | 11/1995 | WO | WO-95 03036 | 2/1995 |
| EP | 0706376 A1 | | 4/1996 | WO | WO 95/03036 | 2/1995 |
| EP | 0 717 041 | | 6/1996 | WO | WO 95/03036 A1 | 2/1995 |
| EP | 0 747 069 | | 12/1996 | WO | WO-95 03083 | 2/1995 |
| EP | 0 797 988 | | 10/1997 | WO | WO 95/03083 | 2/1995 |
| EP | 0 829 238 | | 3/1998 | WO | WO 95/03795 | 2/1995 |
| EP | 0 975 340 | | 2/2000 | WO | WO-95 03795 | 2/1995 |
| EP | 1 407 786 | | 4/2000 | WO | WO-95 15782 | 6/1995 |
| EP | 0 551 182 B1 | | 7/2000 | WO | WO 95/15782 A1 | 6/1995 |
| EP | 1 037 605 | | 9/2000 | WO | WO 96/17629 | 6/1996 |
| EP | 1 090 637 | | 4/2001 | WO | WO 96/20718 | 7/1996 |
| EP | 1140273 B1 | | 10/2001 | WO | WO-96 20718 | 7/1996 |
| EP | 1 159 974 | | 12/2001 | WO | WO 96/25176 | 8/1996 |
| EP | 1 250 166 | | 10/2002 | WO | WO 96/25282 | 8/1996 |
| EP | 1 447 098 | | 8/2004 | WO | WO-96 25282 | 8/1996 |

| | | |
|---|---|---|
| WO | WO 96/38183 | 12/1996 |
| WO | WO-96 38183 | 12/1996 |
| WO | WO 96/39949 A1 | 12/1996 |
| WO | WO 96/39970 A1 | 12/1996 |
| WO | WO 97/01327 | 1/1997 |
| WO | WO-97 01327 | 1/1997 |
| WO | WO 97/17098 A1 | 5/1997 |
| WO | WO 97/26862 | 7/1997 |
| WO | WO-97 26862 | 7/1997 |
| WO | WO-97 31674 | 9/1997 |
| WO | WO 97/31674 | 9/1997 |
| WO | WO 97/33552 | 9/1997 |
| WO | WO 97/41916 | 11/1997 |
| WO | WO-97 41916 | 11/1997 |
| WO | WO 98/11933 A1 | 3/1998 |
| WO | WO 98/14174 | 4/1998 |
| WO | WO 98/15282 A1 | 4/1998 |
| WO | WO 98/24427 | 6/1998 |
| WO | WO-98 24427 | 6/1998 |
| WO | WO 98/25176 | 6/1998 |
| WO | WO 98/25176 A1 | 6/1998 |
| WO | WO-9825176 | 6/1998 |
| WO | WO 98/30249 | 7/1998 |
| WO | WO-98 31415 | 7/1998 |
| WO | WO 98/31415 | 7/1998 |
| WO | WO 98/36784 | 8/1998 |
| WO | WO 98/43618 | 10/1998 |
| WO | WO-98 43618 | 10/1998 |
| WO | WO 98/47540 A1 | 10/1998 |
| WO | WO-99 09729 | 2/1999 |
| WO | WO 99/09729 | 2/1999 |
| WO | WO 99/12577 A1 | 3/1999 |
| WO | WO 99/13916 A2 | 3/1999 |
| WO | WO 99/19004 A2 | 4/1999 |
| WO | WO 99/08729 | 5/1999 |
| WO | WO-99 08729 | 5/1999 |
| WO | WO-99 25336 | 5/1999 |
| WO | WO 99/25336 | 5/1999 |
| WO | WO-99 30684 | 6/1999 |
| WO | WO 99/30684 | 6/1999 |
| WO | WO 99/55396 | 11/1999 |
| WO | WO 99/59556 | 11/1999 |
| WO | WO-99 59556 | 11/1999 |
| WO | WO 99/62510 | 12/1999 |
| WO | WO-99 62510 | 12/1999 |
| WO | WO 00/00023 | 1/2000 |
| WO | WO-00 00023 | 1/2000 |
| WO | WO-00 00238 | 1/2000 |
| WO | WO 00/00238 | 1/2000 |
| WO | WO-00 06152 | 2/2000 |
| WO | WO 00/06152 | 2/2000 |
| WO | WO-00 10552 | 3/2000 |
| WO | 00/21584 A1 | 4/2000 |
| WO | WO 00/32238 A1 | 6/2000 |
| WO | WO 00/32267 | 6/2000 |
| WO | WO-00 47197 | 8/2000 |
| WO | WO 00/47197 | 8/2000 |
| WO | WO-00 50105 | 8/2000 |
| WO | WO 00/50105 | 8/2000 |
| WO | WO 0044414 | 8/2000 |
| WO | WO 0045744 | 8/2000 |
| WO | WO-01 24866 | 4/2001 |
| WO | WO 01/024866 A1 | 4/2001 |
| WO | WO 01/49338 A1 | 7/2001 |
| WO | WO-01 54748 | 8/2001 |
| WO | WO-01 76525 | 10/2001 |
| WO | WO 01/76525 | 10/2001 |
| WO | WO 01/83016 A2 | 11/2001 |
| WO | WO 02/066092 | 8/2002 |
| WO | WO-02 066092 | 8/2002 |
| WO | WO-02 076509 | 10/2002 |
| WO | WO 02/076509 A2 | 10/2002 |
| WO | WO-03 022264 | 3/2003 |
| WO | WO 03/022264 | 3/2003 |
| WO | WO 03/026718 A1 | 4/2003 |
| WO | WO 03/041686 | 5/2003 |
| WO | WO 03/048166 | 6/2003 |
| WO | WO-03 048166 | 6/2003 |
| WO | WO-2004 006976 | 1/2004 |
| WO | WO 2004/006976 | 1/2004 |
| WO | WO-2004 022124 | 3/2004 |
| WO | WO 2004/022124 | 3/2004 |
| WO | WO 04/028582 | 4/2004 |
| WO | WO 2004/028610 | 4/2004 |
| WO | WO-2004 028610 | 4/2004 |
| WO | WO-2005 089855 | 9/2005 |
| WO | WO 2005/089855 | 9/2005 |
| WO | WO-2005 112570 | 12/2005 |
| WO | WO 2005/112570 | 12/2005 |
| WO | WO-2006 023104 | 3/2006 |
| WO | WO 2006/023104 | 3/2006 |
| WO | WO 2008/063576 | 5/2008 |
| WO | WO-2008 063576 | 5/2008 |
| WO | WO 2009/051614 | 4/2009 |
| WO | WO-2009 051614 | 4/2009 |
| WO | WO-2009 051615 | 4/2009 |
| WO | WO 2009/051615 | 4/2009 |
| WO | WO-2009 051616 | 4/2009 |
| WO | WO 2009/051616 | 4/2009 |
| WO | WO 2009/051618 | 4/2009 |
| WO | WO-2009 051618 | 4/2009 |

OTHER PUBLICATIONS

Strecker Ernst Peter Dr Med PR., "Implantable percutaneous endoprosthesis," Espacenet, Publication Date: Jan. 19, 1994; English Abstract of EP-0 578 998.

Judgment of Sep. 16, 2011 (Paper No. 52) from Interference No. 105,787.

Redeclaration of Interference (Paper No. 48) issued Sep. 13, 2011.

Applicants' Amendment of Sep. 12, 2011 (Paper No. 47), filed in U.S. Appl. No. 11/763,125, and cited in the Judgment of Sep. 16, 2011 in Interference No. 105,787.

Online Extract From Sigma-Aldrich Web Site Concerning Poly Vinyl Alcohol (Molecular Weight: MW 500) 2008.

Online Extract From Sigma-Aldrich Web Site Concerning Poly Vinyl Alcohol (Molecular Weight: MS 1700) 2008.

Online Extract From MSDS Online Concerning Sucrose 2007.

Online Extract From Polysciences, Inc. Web Site Concerning Poly Lactic Acid (Molecular Weight: MW 1600 to 2400) 2008.

Online Extract From Polysciences, Inc Web Site Concerning Polyvinylpyrrolidone (Molecular Weight: MW 2500) 2008.

Online Extract From Polysciences, Inc. Web Site Concerning Polycaprolactone (Molecular Weight: MW 2000) 2008.

Online Extract From Polysciences, Inc Web Site Concerning Polycaprolactone (Molecular Weight: MW: 1250) 2008.

Online Extract From Sigma-Alrich Web Site Concerning Poly Actylic Acid (Molecula Weight: MW 1800) 2008.

International Preliminary Examination Report for PCT/DE2003/002871.

Schwartz et al.: "Preclinical Restenosis Models and Drug-Eluting Stents", Journal of the American College of Cardiology, 2004, vol. 44, No. 7, pp. 1373-1385, Elsevier Inc.

Badapulle et al.: "A Hierarchical Bayesian Meta-Analysis of Randomised Clinical Trials of Drug-Eluting Stents", Lancet, 2004, vol. 364, pp. 583-591.

Scheller et al.: "Treatment of Coronary In-Stent Restenosis With a Paclitaxel-Coated Balloon Catheter", The New England Journal of Medicine, 2006, vol. 355, No. 20, pp. 2113-2124.

Licha et al.: "Hydrophilic Cyanine Dyes as Contrast Agents for Near-Infrared Tumor Imaging: Synthesis, Photophysical Properties and Spectroscopic in Vivo Characterization", Phtochemistry and Photobiology, 2000, vol. 72, No. 3, pp. 392-398.

Phillips et al.: "A-Level Biology", Oxford University Press, 1989, pp. 7-8.

English Abstract of WO 92/20718.

Opposition of EP1,666,070.

Opposition of EP1,666,071.

Pschyrembel Klinisches Worterbuch-German Clinical Dictionary and Reference Book by Walter de Gruyter GmbH & Co. KG 1997, p. 717 (Hyperplasia).

"Stent", www.thefreedictionary.com/stent, 2000.

"The Definition of Coated Stent", www.medterms.com. 2003.

"Balloon Catheter", en.wikipedia.org/wiki/balloon_catheter, 2008.

Singla, AK et al.: "Paclitaxel and its Formulations", Int, J. Pharmaceutics 235 (2002): 179-192.

Nuijen, B.et al.: "Progress in the Development of Alternative ..." Investigational New Drugs, 19 (2001): 143-153.

Speck et al., Inhibition of Restenosis in Stented Procine Coronary ..., Invest. Radiol. 2004, 39, 182-186.

Heartwire, January 22, 2003: Drugeluting Stents: Where Are They Now; 2 page, Communication of www.Theheart.Org.

Scheller et al., Addition of Paclitaxel to Contrast Media Prevents Restenosis After Coronary Stent Implanation, J. Am. Coll. Radiol. 2003:42:1415-1420.

Scheller et al., Pactlitaxel Balloon Coating—A Novel Method for Prevention and Therepy of Restenosis; Circulation 2004; 110:810-814.

Li et al., J. Nucl. Med., 38 (7), 1042-47 (1997).

Perflorocarbon Compounds As X-Ray Contrast Media in the Lungs Bulletin Soc, Int. Chic. 1975, 34 (2)137-41.

Paclitaxel: Ein Chemotherapeuticum Zur Restenoseprohylaze? Experimentelle Untersuchengen In Vitro Und In Cico, Zeitschrift Fur Kardiologie,. Band 89, Heft 5 (2000), pp. 390-397.

Herdeg et al., J. Am. Coll. Cardiol. 35 1969-1976.

Baumbach et al. "Local Drug Delivery: Impact of Pressure, Substance Characteristics and Stenting on Drug Transfer into the Arterial Wall, Catherization and Cardiovascular Interventions" 47; pp. 102-106.

Engelmann et al, 2007 International Journal of Pharmaceutics 329, 12-18.

Extracts from the UK Trademarks Register (E7).

Print-out from an online tool for calculating a coefficient of distribution between octanol and water.

Werk et al., "Inhibition of Restenosis in Femoropopliteal Arteries; Paclitaxel-Coated Bersus Uncaoted Calloon ; Femoral Paclitaxel Randomized Pilot Trial", Circulation: Journal of the American Heart Association, 2008, vol. 118, pp. 1358.

Tepe et al., "Local Delivery of Paclitaxel to Inhibit Restenosis During Angioplasty of the Leg", The New England Journal of Medicine, 2008, vol. 358, No. 7, pp. 689-699.

Henry et al., "Poba Plus' : Will the Balloon Regain Its Luster ?", Circulation: Journal of the American Heart Association, 2008, vol. 118, pp. 1309-1311.

English Abstract of CN 1 224 622.

English Abstract of JP11012160.

Final Rejection dated May 1, 2008 in U.S. Appl. No. 10/528,577, filed Mar. 21, 2005.

Non-Final Rejection dated Jul. 2, 2007 in U.S. Appl. No. 10/472,844, filed Sep. 26, 2003.

Final Rejection dated Nov. 1, 2007 in U.S. Appl. No. 10/472,844, filed Sep. 26, 2003.

Non-Final Rejection dated May 29, 2008 in U.S. Appl. No. 10/472,844, filed Sep. 26, 2003.

Final Rejection dated Mar. 4, 2009 in U.S. Appl. No. 10/472,844, filed Sep. 26, 2003.

Non-Final Rejection dated Jan. 15, 2009 in U.S. Appl. No. 10/618,977, filed Jul. 14, 2003.

Non-Final Rejection dated Apr. 20, 2007 in U.S. Appl. No. 10/618,977, filed Jul. 14, 2003.

Nishio et al., "Enhanced Interaction Between Tubulin and Microtubule-Associated Protein 2 Via Inhibition of Map Kinase and CDC2 Kinase by Paclitaxel", Int. J. Cancer; 63, p. 688-693 (1995).

Ding et at, "Association of Mitogen-Activated Protein Kinases with Microtubules in Mouse Macrophages", J. Exp. Med., 183, p. 1899-1904 (1996).

Lieu et al., "Role of Mitogen-Activated Progein Kinase in Taxol-Induced Apoptosis in Human Leukemic U937 Cells", Cell Growhth & Differentiation, 9, p. 767-776 (1998).

Atkins, Peter, "Chapter 7: Simple Mixtures," Physical Chemistry, 6th ed., 1997, pp. 176-186.

Barath et al., "Low Dose of Antitumor Agents Prevents Smooth Muscle Cell Proliferation After Endothelial Injury," JACC, 1989, vol. 13, No. 4, pp. 252A.

Bartoli et al., "In vitro and in vivo Antitumoral Activity of Free, and Encapsulated Taxol," J. Microencapulation, 1990, vol. 7, No. 2, pp. 191-197.

Baron et al., "In vitro Evaluation of c7E3-Fab (ReoPro™) Eluting Polymer-Coated Coronary Stents," Cardiovascular Research, Jun. 2000, vol. 46, pp. 585-594.

BC Lippold, "Retardarzneiformen" in E. Nurnberg, Hagers Handbuch der pharmazeutischen Praxis, vol. 2, Springer-Verlag Berlin Heidelburg New York, 5th edition, 1991, pp. 832-840.

Brunner, H. et al., "Synthesis and in vitro testing of hematoporphyrin type ligands in platinum (II) complexes as potent cytostatic and phototoxic antitumor agents," Inorganica Chimica Acta, 1997, vol. 264, pp. 67-79.

Bult, H., "Restenosis: a challenge for pharmacology," TIPS, Jul. 2000, vol. 21, pp. 274-279.

Consigny, P. Macke et al., "Local Delivery of an antiproliferative drug with use of hydrogel-coated angioplasty balloons," J. Vasc. Interv. Radiol., 1994, vol. 5, pp. 553-560.

Coomber, B. L. et al., "In vitro endothelial wound repair: Interaction of cell migration and proliferation," Arteriosclerosis, Mar. 1990, vol. 10, No. 2, pp. 215-222.

Cox et al., "Effect of Local Delivery of Heparin and Methotrexate on Neointimal Proliferation in Stendted Porcine Coronary Arteries," Coronary Artery Disease, 1992, vol. 3, pp. 237-248.

Cremers et al., "V1742—Paclitaxel-beschictete PTCA-Katheter: Gibt es Unterschiede? Einfluss von Paccocath und Dior Ballonkathetern auf die Neointimaporliferation an Schweinekoronarien," Clin. Res. Cardiol., 1997.

Cremers, B et al., "Comparison of two different paclitaxel-coated balloon catheters in the porcine coronary restenosis model," Clin. Res. Cardiol., 2009, vol. 98, pp. 325-330.

Dichek, D. A. et al., "Seeding of Intravascular stents with genetically engineered endothelial cells," Circulation, 1989, vol. 80, No. 5, pp. 1347-1353.

Dordunoo, S. K. et al., "Release of taxol from poly(ε-caprolactone) pastes: effect of water-soluble additives," Jounral of Controlled Release, 1997, vol. 44, pp. 87-94.

Drachmann et al., "Neoinitimal thickening after stent delivery of paclitaxel: Charge in composition and arrest of growth over six month," J. Am. Coll. Cardiol., 2000, vol. 36, pp. 2325-2332.

Elke M: Kontrastmittel in der radiologischen Diagnostik, pp. 113-119, 3rd edition, Georg Thieme Verlag Stuttgart New York, 1992.

English Translation of Elke M: Kontrastmittel in der radiologischen Diagnostik, pp. 113-119, 3rd edition, Georg Thieme Verlag Stuttgart New York, 1992.

Forth, W. et al. "Allegemeine und spezielle Pharmakologie und Toxikologie," 7 Auflage. Heidelberg: Spektrum Akademischer Verlag, 1996, Chapter, 1, 2, 3.

Garcia-Martinez et al., "Effects of Taxol on Endothelial of the Developing Semilunlar Heart Valves in the Chicken Embryo," Acta Anat, 1988, vol. 133, pp. 282-288.

Gershlick et al., "Inhibition of Restenosis with a Paclitaxel-Eluting, Polymer-Free Coronary Stent: The European evaluation of pacliTaxel Eluting Stent (ELUTES) Trail," Circulation, 2004, vol. 109, pp. 487-493.

Gold, Victor et al., "Amount of Substance Concentration," Compendium of Chemical Technology: International Union of Pure and Applied Chemistry Recommendations, 1987, p. 19.

Grossmann, S, "Neuartige Zubereitungen Hemmung der Neointimaproliferation in verengten Arterien," Dissertation zur Erlangung des akademischen Grades des Doktors der Naturwissenschaften (Dr. rer. nat.), Nov. 2006.

Hamm, C. W. et al., "Guideline: Diagnostic Heart Catheter Examination," Clin Res Cardiol, 2008, vol. 97, pp. 475-512.

English Translation of Hamm, C. W. et al., "Guideline: Diagnostic Heart Catheter Examination," Clin Res Cardiol, 2008, vol. 97, pp. 475-512.

Hiatt, "Drug-Eluting Stents for the Prevention of Restenosis: In Quest for the Holy Grail," Catheterization and Cardiovascular Interventions, vol. 55, pp. 409-417, 2002.

Hou, D. et al., "Intrapericardial paclitaxel delivery inhibits neointimal proliferation and promotes arterial enlargement after porcine coronary overstretch," Circulation, 2000, vol. 102, pp. 1575-1581.

Indolfi et al., "Smooth Muscle Cell Proliferation is Proportional to the Degree of Balloon Injury in a Rat Model of Angioplasty," Circulation, 1995, vol. 92, pp. 1230-1235.

Kalbitz et al., "Modulation der Wirkstoffpenetration in die Haut," Pharmazie, 1996, vol. 51, pp. 619-637.

Kandarpa et al., "Mural Delivery of Iloporst with Use of Hydrogel-coated Balloon Catheters Suppresses Local Platelet Aggregation," J. Vasc. Inter. Radiol., Nov./ Dec. 1997, vol. 8, pp. 997-1004.

Kandarpa et al., "Site-specific Delivery of Iloprost during Experimental Angioplasty Suppresses Smooth Muscle Cell Proliferation,"J. Vasc. Inter. Radiol., May/ Jun. 1998, vol. 9, pp. 487-493.

Katsuda et al., "The Role of Cytoplasmic Microtubules in Regulation of Smooth Muscle Proliferation," Clin. Ter. Cardiovasc.,1990, IX(4), pp. 245-248.

Khan, I. A. et al., "The Intra-vascular stent as a site-specific local drug delivery system," Drug Development and Industrial Pharmacy, 2005, vol. 31, pp. 59-78.

Kirk-Othmer, Encyclopedia of Chemical Technology, 3$^{rd}$Edition, vol. 17, 1982, John Wiley & Sons, pp. 281-310.

Lamba, Nina M. K. et al., "Structure and Physical Characterization of Polyurethanes," Polyurethanes in Biomedical Applications ,Ch. 4, pp. 43-52, 1998, CRC Press.

Langer, R., "New methods of drug delivery," Science, Sep. 28, 1990, vol. 249, pp. 1527-1533.

Leo, Albert et al., "Partition Coefficients and Their Uses," Chemical Reviews, Dec. 1971, vol. 71, No. 6, pp. 525-616.

Liggins, Richard T. et al., "Paclitaxel loaded poly(L-lactic acid) microspheres: properties of microspheres made with low molecular weight polymers," International Journal of Pharmaceutics, 2001, vol. 222, pp. 19-33.

Liggins, R. T. et al., "Solid-State Characterization of Paclitaxel,"J. Pharma. Sci., 1997, vol. 86, pp. 1458-1463.

Lübbe, A. S. et al., "Preclinical experiences with magnetic drug targeting: Tolerance and Efficacy," Cancer Research, 1996, vol. 56, pp. 4694-4701.

Manderson et al., "Balloon Catheter Injury to Rabbit Cartoid Artery. I. Changes in smooth muscle phenotype," Artheriosklerosis, 1989, vol. 9, pp. 289-298.

Matthew, R. T. et al., "Synthesis and Evaluation of Some Water-Soluble Prodrugs and Derivatives of Taxol with Antitumor Activity," J. Med. Chem., 1992, vol. 35, pp. 141-151.

Mitchel et al., "Inhibition of Platelet Deposition and Lysis of Intrcoronary Thrombus during Balloon Angioplasty using Urokinase-Coated Hydrogel Balloons," Circulation, Oct. 1994, vol. 90, pp. 1979-1988.

Mortimer, C. et al., Basiswissen Chemie (excerpt) (1987).

Muller et al., "Colchicine and Antineoplastic Therapy for the Prevention of Restenosos after Percutaneous Coronary Interventions," JACC, 1990, vol. 17, No. 6, pp. 126B-131B.

Nairn, John A., "Polymer Characterization," Materials Science & Engineering 5473, 2003, Ch. 3, pp. 43-55.

Nicolaou, K. C. et al., "Design, synthesis and biological activity of protaxols," Nature, Jul. 29, 1993, vol. 364, pp. 464-466.

Parker, Sybil P., "Micelle," McGraw-Hill Encyclopedia of Chemistry—Second Edition, 1992, pp. 638-639.

Sangster, J. et al., Octanol-Water Partition Coefficients: Fundamentals and Physical Chemistry, 1997, vol. 2 of Wiley Series in Solution Chemistry, pp. 1-49.

Schmitz, S. A. et al., "Superparamagnetic iron oxide-enhanced MRI of atherosclerotic plaques in Watanabe Hereditable Hyperlipidemic Rabbits," Investigative Radiology, Aug. 2000, vol. 35, No. 8, pp. 460-471.

Sharma, U. S. et al., "Pharmaceutical and Physical Properties of Paclitaxel (Taxol) Complexes with Cyclodextrins," J. Pharma. Sci., 1995, vol. 84, pp. 1223-1230.

Slepian, from Textbook of Interventional Cardiology, 1990, Section IV, Chapter 32, pp. 647-670.

Sollott, Steven J. et al., "Taxol Inhibits Neointimal Smooth Muscle Cell accumulation after angioplasty in the rat," The Journal of clinical Investigation, Apr. 1995, vol. 95, pp. 1869-1876.

Speck, Ulrich—German Priority Document for file No. 101 15 740.1 filed on Mar. 26, 2001.

Swindell, C.S. et al., "Biologically Active Taxol Analogues with Deleted A-ring Side Chain Substituents and Variable C-2' Configurations," J. Med. Chem, 1991, vol. 34, pp. 1176-1184.

Tarr, B. D. et al., "A New Parenteral Vehicle for the Administration of Some Poorly Water Soluble Anti-Cancer Drugs," J. Parent Sci. Technol., 1987, vol. 41, pp. 31-33.

Tawashi, R. "The dissolution rates of crystalline drugs," J. Mond. Pharm. 1968, vol. 4, No. 11, pp. 371-379.

Ulicky, L. et al., "Nernst's Distribution Law," Comprehensive Dictionary of Physical Chemistry, pp. 266-267, 1992.

Van Belle, E. et al., "Passivation of metallic stents after arterial gene transfer of phVEGF165 inhibits thrombus formation and intimal thickening," J. Am. Coll. Cardiol., 1997, vol. 29, pp. 1371-1379.

Voigt, R., Lehrbuch der pharmazeutishchen Technologie, 5$^{th}$ edition, VEB Verlag Volk and Gesundheit Berlin, 1984, p. 689.

Voisard et al., "The In-vitro Effect of Antineoplastic Agents on Proliferative Activity and Cytoskeletal Components of Plaque-Derived Smooth-Muscle Cells from Human Coronary Arteries," Coronary Artery Disease, 1993, vol. 4, pp. 935-942.

Wichert, B et al., "Low Molecular weight PLA: a suitable polymer for pulmonary administered microparticles?" J. Microencapsulation, 1993, vol. 10, No. 2, pp. 195-207.

Yushmanov, Victor E. et al., "Dipyridamole Interacts with the Polar Part of Cationic Reversed Micelles in Chloroform: 1H NMR and ESR Evidence," Journal of Colloid and Interface Science, 1997, vol. 191, pp. 384-390.

Clinical Cardiology Divergent Effects on Coronary Artery Disease: Abstract from 70$^{th}$ Scientific Session: Circulation, vol. 96, No. 8, Oct. 21, 1997.

Abstracts From the 70$^{th}$ Scientific Sessions, Circulation, Oct. 21, 1997, 96 Suppl. 1: 1-288.

English Abstract of CN 1 224 622, Aug. 4, 1999.

English Abstract of DE 19514104, Stemberger, Axel, Dr., "Coating for bio-material insertable into the bloodstream or tissue of the human body," Nov. 28, 1996.

English Abstract of DE 69925936, Stemberger, Axel, Dr., "High efficiency local drug delivery," May 11, 2006.

English Abstract of DE 4435652, Stemberger, Axel Dr., "Coating for bio-material to be used e.g. as sutures," Apr. 11, 1996.

English Abstract of EP 0 551 182, Morris, R. E. et al., "Method of treating hyperproliferative vascular disease using rapamycin, eventually in combination with mycophenolic acid," Jul. 14, 1993.

English Abstract of JP-06-063145, "Balloon Catheter for intravascular dosing," BUAAYU KK, Patent Abstracts of Japan, Publication Date: Mar. 8, 1994.

English Abstract of JP-06-063145, "Balloon Catheter for Intravascular dosing," BUAAYU KK, Thomson Innovation, Publication Date: Mar. 8, 1994.

English abstract of JP-07-500585, Thomson Innovation, Patent Record View, Publication Date: Jan. 19, 1995.

English Abstract of JP-07-328124, "Medicine dosing catheter," Terumo Corp., Patent Abstracts of Japan, Publication Date: Dec. 19, 1995.

English abstract of JP-10-509691, Thomson Innovation, Patent Record View, Publication Date: Sep. 22, 1998.

English Abstract of JP-11-012160, Jan. 19, 1999.

English Translation of Jp 36371777, Thomson Innovation, Publication Date: Mar. 23, 2005.

Patent Family Listing for JP-2001 508320 (Publication Date: Jun. 26, 2001), Thomson Innovation.

Patent Family Listing for JP-2002 536058 (Publication Date: Oct. 29, 2002), Thomson Innovation.

English Abstract of WO 92/20718, Nov. 26, 1992.

English Abstract of WO 96/25282, Kaufmann, G. et al., "Process for producing a plastic cladding component and cladding component produced especially by said process," Aug. 22, 1996.

Office Action issued Apr. 20, 2007 in U.S. Appl. No. 10/618,977, filed Jul. 14, 2003.

Office Action issued Oct. 13, 2011 in U.S. Appl. No. 11/763,116.

Office Action issued Aug. 16, 2011 in U.S. Appl. No. 12/835,420.

Office Action issued May 23, 2011 in U.S. Appl. No. 12/835,414.

U.S. Appl. No. 08/094,536 (Priority of D2).

U.S. Appl. No. 08/062,451 (Priority of D3).

English translation of Decision of Final Rejection, Japanese Application No. JP 2004-235694, issued Mar. 9, 2010.
Office Action issued Feb. 22, 2010 in U.S. Appl. No. 10/528,577.
Notice of Allowance issued Aug. 23, 2010 in U.S. Appl. No. 10/528,577.
Notice of Allowance issued Dec. 9, 2010 in U.S. Appl. No. 10/528,577.
Notice of Allowance issued Nov. 28, 2011 in U.S. Appl. No. 10/528,577.
Notice of Allowance issued Jun. 25, 2012 in U.S. Appl. No. 10/528,577.
Office Action issued Dec. 6, 2011 in U.S. Appl. No. 12/835,414.
Office Action issued May 9, 2012 in U.S. Appl. No. 12/835,414.
Office Action issued Mar. 9, 2012 in U.S. Appl. No. 12/835,420.
Notice of Allowance issued May 24, 2012 in U.S. Appl. No. 12/835,420.
Office Action issued Apr. 29, 2009 in U.S. Appl. No. 11/763,116.
Office Action issued Sep. 18, 2009 in U.S. Appl. No. 11/763,116.
Office Action issued Apr. 8, 2010 in U.S. Appl. No. 11/763,116.
Office Action issued May 7, 2012 in U.S. Appl. No. 11/763,116.

* cited by examiner

MEDICAL DEVICE FOR DISPERSING MEDICAMENTS

This application is a divisional of U.S. patent application Ser. No. 10/528,577, filed Mar. 21, 2005, now U.S. Pat. No. 8,257,305, which is incorporated by reference herein, which in turn is a U.S. National Stage Filing under 35 U.S.C. §371 of International Patent Application No. PCT/DE2003/002871, filed on Aug. 26, 2003, and published as WO 2004/028582 A1 on Apr. 8, 2004, which in turn claims priority under 35 U.S.C. §119 of German Patent Application No. DE 102 44 847.7, filed Sep. 20, 2002.

This invention relates to a medical apparatus that releases drugs for the selective therapy of specific tissues or organ parts and to a method of manufacturing such drug-coated devices.

Numerous diseases do not affect the entire organism at the same time but are restricted to specific tissues, often even to very limited individual tissue areas or organ parts. Examples can be found among tumor, joint and vascular diseases.

Pharmacotherapy of such diseases generally is effected by oral or intravenous administration of drugs that spread throughout the body and cause undesirable side effects in healthy tissues and organs, especially when the disease to be treated is in a severe stage, which limit the therapeutic application. The diseased tissues could be treated either selectively using drugs that specifically bind to diseased tissue (e.g. antibodies) while the administration path is maintained, or by selective administration, e.g. direct injection into the diseased tissue or supply via a catheter to the blood vessels that feed the diseased tissue. In case of selective administration may problems arise due to the short period of time during which the drugs are efficacious and the invasive administration paths, as repeated administration is not an option. When drugs are selectively administered via the bloodstream that feeds the diseased tissue, there is the additional problem that the drugs are insufficiently extracted when the blood or active agent solution swiftly flows through the blood vessels.

These problems used to be addressed by various pharmaceutical preparations with sustained release of the active agent, drug-releasing implants or selective access paths that stay operational for a longer period of time such as implanted catheters, etc.

It is known that the surface of medical equipment inserted into the body, in particular, of catheters, can be coated with agents that enhance gliding quality or prevent blood coagulation but have no therapeutic effect.

In addition, catheters are equipped with special devices for injecting drugs into the arterial wall, for example, using needles or a perforation of the catheter wall that sits adjacent to the vessel wall and through which the drug is injected at high pressure.

Other principles are based on extending the contact time between the arterial wall and an active agent preparation administered via the catheter by either blocking the blood flow for a sufficient period of time, e.g. using dual balloon catheters in which the active agent solution is contained in a chamber between the balloons, or by voids between a toric outer wall of the balloon allowing a limited flow of blood through a canal that passes through the balloon.

According to U.S. Pat. No. 5,102,402, drugs in the form of microcapsules are inserted into preformed recesses of balloon catheters for delayed release of the active agent. When the balloon is inflated, the microcapsules are to be pressed against the vessel wall, remain there and slowly release the active agent(s). Many authors propose to apply drugs embedded in hydrogel onto balloon catheters while they do not specify the function of the hydrogel, i.e. to act as an adhesive, to improve the gliding quality, or for controlled drug release.

A disadvantage of the products mentioned above is their complex structure, which causes production, quality control, and cost problems and forces additional aggravating working steps on doctors and patients when applied. Some of the methods mentioned may result in undesirable vascular damage in excess of the intended dilatation of the vessel. Another setback is that each measure aimed at extending contact time entails another reduction in blood and oxygen supply to the downstream tissues.

For the sake of completeness, we also refer to a device for preventing restenosis as described in WO 01/24866 that is coated with a lipid ceramide substance derived from natural cell membranes. This substance is used because of its affinity to cell walls that is not found in common drugs. Experts in the field continue to state that restenosis prevention using drugs requires release of the active agent over a period of several days.

The problem underlying the present invention is to provide a device for the release of drugs into specific tissue areas or organ parts that has a strong therapeutic effect without damaging healthy tissue, which is sufficiently well tolerated, and can be produced and applied with a minimal effort.

This problem is solved according to the invention by a device designed or produced in accordance with the characteristics of claims 1 and 15. The subordinate claims disclose further characteristics and advantageous improvements of the invention.

The invention provides improved drug-carrying balloon catheters or similar medical devices manufactured in a simple process that are highly versatile and facilitate the immediate release of active agents. Surprisingly, and contrary to the currently acknowledged opinion, no continuing release of the active agent from an inert matrix (polymer, hydrogel, microcapsule, etc.) and no special chemical or physical state of the active ingredients is required or useful. Therefore, no sophisticated techniques for producing or controlling depot formulations are required.

Coating balloons on catheters with drugs according to this invention is particularly useful because there is a frequent need for treatment after blood vessels or other passages in the body were dilated with balloons to prevent stenosis or an occlusion of the lumen created by the pressure of the balloon, to limit tumor growth or to enhance healing processes including the formation of collateral circulation. This can be achieved by drugs that become effective in the immediate vicinity of the balloon surface. The drugs firmly adhere to the balloon while passing through arteries with an intense blood flow on their way to their target until the balloon is inflated, and an effective dose is released in the short time (sometimes just a few seconds) during which the inflated balloon is in contact with the tissue, absorbed by the tissue in such a way that the blood flow that resumes immediately after the balloon is deflated does not rinse it off.

The subjects for coating are wires of the invention used to guide catheters, needles and catheters or catheter parts that are pressed against the diseased tissue at least for a short time. Preferred catheter materials are polyamides, polyamide mixtures and copolymers, polyethylene terephthalate, polyethylene and copolymers, polyurethane, natural rubber and its derivatives. The lengths and diameters of the catheter or balloon areas designated for pharmacological treatment are not of any decisive importance for their application as the dosage is calculated in μg of active agent/mm$^2$ of surface area. For example, balloons with diameters ranging from 2 to 4 mm and lengths ranging from 1.0 to 4.0 cm are commonly used for coronary dilatation. Balloons up to >20 mm in diameter and up to >10 cm in length can be used for other vessels. The surfaces to be coated may be smooth (i.e. without a special structure for absorbing the active agents), roughed up or comprise any structure; while no special surface structures are required for the active agents to adhere, such structures also do not impede adhesion. Adhesion of the active agents to the balloon surfaces is exclusively caused by selecting suitable solvents and, optionally, adding substances that influence adhesion. It is even surprisingly strong on completely smooth balloon surfaces.

All surfaces can additionally be coated with substances that improve the gliding quality of the products, prevent blood from coagulating on the surface or improve any other properties of these medical products have but the materials used for coating do not have to be released into the environment and this additional coating does not noticeably reduce the release of the active agents for treatment of the target tissue and thus the product's efficacy.

Balloon catheters are formed by dilating a segment of 1 cm to ca. 10 cm length of very thin plastic tubes. The dilated, very thin-walled balloon membrane is then folded several times along the catheter axis and wrapped tightly around the catheter axis so that the dilated area, when folded, is only slightly greater in diameter than the rest of the catheter. The tight folding of the balloon membrane is required for passing the balloon catheter through access ports, guiding catheters and heavily stenosed sections of blood vessels.

The balloons of catheters can be coated when folded or when unfolded. The process always provides an intact and sufficiently uniform surface coating, and the active agents adhere to the surface of the balloon catheter even when it is refolded after being coated when unfolded.

A balloon that was coated when unfolded is produced without any impact on the coating, for example by using balloon membranes with preformed folds and bends whose structure is not lost due to dilatation and which allow the balloon membrane to refold at least loosely when the pressure is discharged from the balloon without requiring an external force as primary cause. It is only after this prefolding that the preformed folds are compressed by external pressure or by a vacuum. Folds are in no way required to hold the active agent. In addition refolding can be achieved using minor mechanical force by very smooth materials, and the tools used may also be wetted by slippery biocompatible liquids in which the active ingredients do not or, at least, do not well dissolve.

In accordance with another variant of the invention, the balloons of readily folded balloon catheters are coated by dipping them into low-viscosity active agent solutions. Solvent and active agent penetrate into the extremely dense folds where they form a surprisingly uniform coat that contains a reproducible dose and is not damaged by any subsequent step. The solution or, after the solvent has dried, the coat that adheres to the outer surface may be left there or may be removed in another step so that only the active agent portion that sits inside the folds of the balloon is retained.

After coating, when the balloon is folded, a stent can be pulled over the balloon catheter and firmly pressed onto it. The only step still required is sterilization, e.g. using ethylene oxide.

The work cycle laid out like this is extremely simple, hardly susceptible to failures, and can be carried out even with mechanically, chemically and physically sensitive coating materials. It was found that coating using this method does not result in any undesirable loosening or sticking together of the folds and that the active agent applied in this way adheres firmly enough to not be rinsed off by the bloodstream but releases most of the active agent when the balloon is inflated in the target tissue.

Suitable drugs are lipophilic, mostly water-insoluble and strongly acting drugs that bind to any tissue components. Drugs are called lipophilic when their butanol to aqueous buffer solution (pH 7) distribution ratio is 0.5, preferably 1 and particularly preferred 5, or when their octanol to aqueous buffer solution (pH 7) distribution ratio is 1, preferably 10, and particularly preferred greater than 50. Alternatively, or in addition to this, the drugs should reversibly and/or irreversibly bond to cell components at percentages greater than 10%, preferably greater than 50%, and particularly preferred greater than 80%. Preferred are substances that inhibit cell proliferation or inflammatory processes, or antioxidants such as Paclitaxel and other taxanes, Rapamycin and related substances, tacrolimus and related substances, corticoids, sexual hormones (estrogen, estradiol, antiandrogens) and related substances, statins, epothilones, probucol, prostacyclins, angiogenesis inducers, etc.

These substances are preferably present as a dry solid or as an oil on the surfaces of the various medical products. Preferred are the smallest particle sizes (mostly <5 microns, preferably <1 microns, particularly preferred <0.1 microns), particularly preferred are amorphous non-crystalline structures of the finest particle size that dissolve fast upon contact with tissue due to their large surface area and despite the generally poor water-solubility of the drugs and do not function as microcapsules, i.e. dissolve spontaneously and fast. It is sufficient that an effective dose is present in the form of smallest or amorphous particles; larger particles hardly contribute to the active agent concentration in the tissue but do not cause any interference. The dosage depends on the desired effect and the efficacy of the drug used. It may be up to 5 $\mu g/mm^2$ and this value does not even constitute an upper limit. It is easier to handle smaller dosages.

Good adhesion to the surfaces of catheters, needles or wires on an improved absorption by the tissues is achieved by embedding strongly lipophilic active agents with poor water solubility in a readily water-soluble matrix substance. Suitable matrix substances are low-molecular (molecular weight <5000 D, preferably <2000 D) hydrophilic substances such as contrast agents and dyes used in vivo for various diagnostic procedures in medicine, sugar and related substances such as sugar alcohols, low-molecular polyethylene glycols, biocompatible organic and inorganic salts such as, for example, benzoates, salts and other derivatives of salicylic acid, etc. Examples of contrast agents are iodinated X-ray contrast agents and paramagnetic chelates, examples of dyes are indocyanine green, fluorescein, and methylene blue. Excipients may also improve shelf life of the products, cause specific additional pharmacological effects or be instrumental for quality control.

In another embodiment of the invention, the pharmaceutical active agents can be adsorbed to particles or applied to the surfaces of suitable medical products with a low-molecular matrix. Suitable particles once again are diagnostics known to be biocompatible such as ferrites and various contrast agents for sonography.

Excipients of any kind can be used at lower or higher doses than the active ingredients.

The medical products are coated using solutions, suspensions, or emulsions of the drugs and excipients mentioned above. Suitable media for solution, suspension or emulsion are, for example, ethanol, isopropanol, ethyl acetate, diethyl ether, acetone, dimethyl sulfoxide, dimethyl formamide, glycerin, water or mixtures thereof. Solvent selection is based on the solubility of the active agents and adjuvants, the wetting of the surfaces to be coated and the effect on the structure of the coating and particles remaining after evaporation of the solvent, their adhesion to the surface and active agent transfer to the tissue in very short contact times.

Coating can be carried out by immersing, spreading, applying with devices which deliver a defined volume to the surface or spraying at various temperatures and, optionally, vapor saturation of the solvents in the atmosphere. The procedure can be repeated several times using different solvents and excipients as may be required.

The balloons of folded balloon catheters ready for use can be given a surprisingly uniform, reproducible, dose-controllable coating without impairing catheter functionality by immersing them in solutions containing the active agent(s) or by other measures. When the balloons are repeatedly immersed in unsaturated active agent solutions, the active agent applied previously is not completely stripped off; instead, the active agent content of the balloons is increased in a reproducible manner.

Excess solution or excess substances from the coating solution that are loosely attached to the exterior can be removed with simple methods without impairing the efficacy of the coating.

The various types of medical devices designed and manufactured according to the invention come into short-term contact with the tissue, i.e. for a few seconds, minutes, or hours. It is desirable in some cases to pharmacologically treat the tissue with drugs in the immediate vicinity of the medical product, e.g. to prevent excess growth as a response to an injury or to reduce tumor growth, to enhance neovascularization or diminish inflammatory reactions. In all these cases, high local drug concentrations can be achieved for an astonishingly long time using the method described above. A major advantage is the extraordinary versatility of uses of the products and methods described.

A preferred application is to reduce hyperproliferation of vessel walls induced by dilatation with balloon catheters. This can be achieved when stents are implanted by coating these stents with drugs, but only for the vessel section covered by the stent. The coated balloon catheters also treat any areas at short distance in front of and just behind the stent that need treatment, they can treat the section where a stent has been implanted without requiring another stent implantation and vessels in which no stent is to be or can be implanted. An advantage as compared to the stents that release a drug over a long period of time is improved healing and simultaneous good inhibition of hyperproliferation and a reduced risk of thrombosis.

Several embodiments of the invention will be described below with reference to examples regarding the coating of balloon catheters, adhesion of the coating in the bloodstream, restenosis inhibition and active agent content of the catheters.

EXAMPLE 1

Coating an Expanded Balloon Catheter with Paclitaxel in Ethyl Acetate

Balloon catheters made by BMT, Oberpfaffenhofen/Munich, Germany, product name Joker Lite, balloon dimensions 2.5 mm by 20 mm, are inflated to the maximum and immersed full length for 1 minute in ethyl acetate, 18.8 mg Paclitaxel per ml, +1% pharmaceutical olive oil, dried: Paclitaxel content 39 micrograms (after extraction with ethanol, HPLC).

EXAMPLE 2

Coating a Folded Balloon Catheter with Paclitaxel in Ethyl Acetate

Balloon catheters made by BMT, Oberpfaffenhofen/Munich, Germany, product name Joker Lite, balloon dimensions 2.5 mm by 20 mm, are immersed full length in folded condition for 1 minute in ethyl acetate, 18.8 mg Paclitaxel per ml, +1% pharmaceutical olive oil, and dried:
Paclitaxel content 69 micrograms.

EXAMPLE 3

Coating a Folded Balloon Catheter with Paclitaxel in Ethyl Acetate a) Balloon catheters made by BMT, Oberpfaffenhofen/Munich, Germany, product name Joker Lite, balloon dimensions 2.5 mm by 20 mm, are immersed full length in folded condition for 1 minute in ethyl acetate, 16.6 mg Paclitaxel per ml, and dried for 4 hours:
Paclitaxel content 54 micrograms.
b) Same procedure, but additional two times immersed for 5 seconds with 1 hour drying time after each immersion process in solution A (=3.33 ml ethyl acetate+100.0 mg of Paclitaxel): Paclitaxel content 126 micrograms.
c) Same procedure, but additional four times immersed for 5 seconds with 1 hour drying time after each immersion process in the same solution:
Paclitaxel content 158 micrograms.

EXAMPLE 4

Coating a Balloon Catheter with Paclitaxel in Acetone

Dissolve 350 mg of Paclitaxel in 9.0 ml of acetone; balloon catheters made by BMT, Oberpfaffenhofen/Munich, Germany, product name Joker Lite, balloon dimensions 2.5 mm by 20 mm, are inflated to the maximum and immersed full length for 1 minute and removed. The solvent is dried for 12 hours at room temperature. Then the balloon is deflated and folded in the common way using a PTFE-coated tool. Optionally, one can crimp a stent of suitable dimensions onto the balloon: 29 micrograms of Paclitaxel on the balloon.

EXAMPLE 5

Coating a Balloon Catheter with Paclitaxel in Acetone a) Immersion of folded balloon catheters made by BMT, product name Allegro, balloon dimensions 2.5 by 20 mm in a mixture of 0.15 ml ethanol+4.5 µl of Ultravist 300 (an X-ray contrast agent made by Schering AG, Berlin, Germany)+1.35 ml of acetone+0.8 mg of Sudan red+30.0 mg of Paclitaxel:
The folded balloon sections of the catheters are immersed 5 times, the first time for one minute, then dried for 3 hours, then 4 times at 1 hour intervals for 5 seconds each; subsequently, a stent was crimped on and the catheter was sterilized in the common way using ethylene oxide:
Paclitaxel content 172 micrograms, no decomposition products of the active agent were determined using HPLC b) A saturated aqueous mannitol solution is used instead of Ultravist 300
c) A saturated aqueous sodium salicylate solution (pH 7.5) is used instead of Ultravist 300
d) 5 mg of acetylsalicylic acid are added to the completed solution according to (5a).
e) 5 mg of glycerin are added to the completed solution according to (5a).

EXAMPLE 6

Adhesion of the Active Agent in the Bloodstream 12 balloon catheters made by BMT, product name Allegro, balloon dimensions 2.5 by 20 mm, were used. The folded balloon sections of 6 catheters each were either 5 times immersed in [0.15 ml of ethanol+4.5 µl of Ultravist 300+1.35 ml of acetone+0.8 mg of Sudan red+30.0 mg Paclitaxel] or 5 times in [1.5 ml of ethyl acetate+0.8 mg Sudan red+31.0 mg Paclitaxel], the first time for 1 minute each with 3 hours of drying time, then 4 times for 5 seconds each at 1 hour intervals; then 3 of the folded balloons of each group were gently moved for 5 minutes at 37° C. in 50 ml of human blood and removed to determine the Paclitaxel content: Reduction of mean values (n=3 per coating method) by 5 minutes of movement in blood as compared to 3 control catheters that were not incubated in blood.
Acetone: 12%
Ethyl acetate: 10%

EXAMPLE 7

Examination of restenosis inhibition after angioplasty and stent implantation in coronary arteries of pigs.
Folded balloon catheters of the Joker Lite type made by BMT, 3.5 by 20 mm or 3.0 by 20 mm were immersed for 1 minute either in
solution A) 3.33 ml of ethyl acetate (EA)+100.0 mg of Paclitaxel, or in
solution B) 0.45 ml of ethanol+100 µl of Ultravist-370+4.5 ml acetone (ac)+150.0 mg Paclitaxel
and dried over night at room temperature. One more (low dose=L) or 4 more (high dose=H) immersion process(es), respectively, were carried out for just five seconds at 1 hour intervals on the next day.
Active agent content after 2 immersions in solution (B) averaged 250 µg, after 5 immersions in solution (B) 500 µg, in solution (A) 400 µg.
The catheters coated with Paclitaxel or uncoated were used to implant stents into the left anterior or lateral coronary artery of a total of 22 pigs, and the vessels were slightly overdilated to stimulate restenosis by tissue hyperplasia. The animals were reangiographed after 5 weeks, and the vessel stenosis shown in the angiograms was measured using an automatic computer program.

| Group | Stenosis (%) |
|---|---|
| Uncoated | 50.49 |
| AcL | 20.22 |
| EAH | 36.01 |
| AcH | 0.86 |
| P | .004 |

Quantitative coronary angiography 5 weeks after stent implantation with uncoated and coated catheters; stenosis=reduction of lumen diameter in percent in the area of the stent as compared to the lumen diameter immediately after stent implantation; mean value and statistical significance of the effect of treatment.

EXAMPLE 8

Active Agent Content of the Catheters after Vessel Dilatation and Stent Implantation After stent implantation and removal from the animals, the balloons from Example 8 ca. 3 cm in length were cut off the balloon catheters and placed in 1.5 ml of ethanol. Paclitaxel content was determined using HPLC. All available coated balloons and a selection of uncoated balloons were examined. Coronary,

| | | |
|---|---|---|
| 3.0 by 20 mm, coating: | Ac high | 38 ± 4 µg (n = 4) |
| | Ac low | 22 ± 5 µg (n = 2) |
| | EEE high | 41 (n = 1) |
| 3.5 by 20 mm, coating: | Ac high | 37 ± 10 µg (n = 8) |
| | Ac low | 26 ± 6 µg (n = 8) |
| | EEE high | 53 ± 9 µg (n = 9) |
| Uncoated (independent of size and vessel area) | | 0.9 ± 1.0 µg (n = 7) |

It follows from Example 6 that a maximum of 10% of the dose is lost before the balloon is inflated and about 10% of the dose remain on the balloon.

EXAMPLE 9

Probucol is added to acetone at a concentration of 100 mg per ml; the solution is used to coat balloon catheters as described in the above examples.

EXAMPLE 10

Rapamycin is dissolved at a concentration of 10 mg/ml in diethyl ether. The balloon sections of the catheters are coated as described in the above examples; after removal from the coating solution, the balloons should be brought into a horizontal position and continuously be turned around their longitudinal axis as soon as possible.

EXAMPLE 11

Epothilone B is dissolved in ethyl acetate at a concentration of 2 mg/ml; the solution is used to coat balloon catheters as described in the above examples.

The invention claimed is:
1. A balloon catheter medical device comprising:
a balloon surface having paclitaxel embedded in a low-molecular weight matrix substance adhered thereto and dried,
wherein the dried paclitaxel is immediately releasable after coming into contact with tissue.
2. The medical device according to claim 1, wherein said low-molecular weight matrix substance has a molecular weight of less than 5000 D and is selected from contrast agents and dyes used in vivo, sugars, sugar alcohols, low-molecular polyethylene glycols, and biocompatible organic and inorganic salts.
3. The medical device according to claim 1, wherein said low-molecular weight matrix substance is selected from iodi- nated X-ray contrast agents, paramagnetic chelates, indocyanine green, fluorescein, and methylene blue.

4. The medical device according to claim 1, wherein said low-molecular weight matrix substance is a readily water-soluble hydrophilic matrix substance.

5. The medical device according to claim 1, wherein the low-molecular weight matrix substance has a molecular weight of less than 5000 D.

6. The medical device according to claim 1, wherein the lowe-molecular weight matrix substance has a molecular weight of less than 2000 D.

7. The medical device according to claim 1, wherein said balloon catheter medical device further comprises a stent.

8. The medical device according to claim 1, wherein the balloon catheter medical device does not comprise a stent.

9. The medical device according to claim 1, wherein the balloon surface has preformed longitudinal folds maintaining an inclination to refold after inflation.

10. The medical device according to claim 9, wherein at least an area covered by the folds is covered with the paclitaxel.

11. The medical device according to claim 9, wherein only an area covered by the folds is covered with the paclitaxel.

12. The medical device according to claim 1, wherein the balloon surface consists of a very smooth material to which the paclitaxel embedded in the low-molecular weight matrix substance adheres sufficiently well to resist forces required for folding, essentially without damage.

13. The medical device according to claim 1, wherein the balloon surface is coated by immersion in a low-viscosity pacitaxel solution while in a fully folded condition.

14. The medical device according to claim 1, wherein the paclitaxel is present as a dry solid on the balloon surface.

15. The medical device according to claim 14, wherein an effective dose of the paclitaxel includes amorphous structures with particle sizes ranging from <0.1 micron to 5 microns that dissolve quickly due to their large surface area and despite the poor water-solubility of the paclitaxel.

16. The medical device according to claim 1, wherein matrix the low-molecular weight matrix substance is hydrophilic.

17. The medical device according to claim 1, wherein the paclitaxel is applied to the balloon surface with said low-molecular weight matrix substance.

18. The medical device according to claim 1, wherein the balloon surface further comprises a substance that influences the gliding quality of the device or that prevents blood coagulation.

19. A balloon catheter medical device comprising:
a balloon surface having a lipophilic proliferation inhibitor, a lipophilic inflammation inhibitor, or a lipophilic antioxidant adhered thereto, wherein the lipophilic proliferation inhibitor, the lipophilic inflammation inhibitor, or the lipophilic antioxidant is embedded in a low-molecular weight matrix substance, applied thereon to the balloon surface and dried, and
wherein the dried lipophilic proliferation inhibitor, the dried lipophilic inflammation inhibitor, or the dried lipophilic antioxidant is immediately releasable after coming into contact with tissue.

20. The medical device according to claim 19, wherein said the lipophilic proliferation inhibitor, the lipophilic inflammation inhibitor, or the lipophilic antioxidant is selected from taxanes, Rapamycin, tacrolimus, corticoids, sexual hormones, statins, epothilones, probucol, prostacyclins, and angiogenesis inducers.

* * * * *

UNITED STATES PATENT AND TRADEMARK OFFICE
CERTIFICATE OF CORRECTION

| | | |
|---|---|---|
| PATENT NO. | : 8,439,868 B2 | Page 1 of 1 |
| APPLICATION NO. | : 12/782989 | |
| DATED | : May 14, 2013 | |
| INVENTOR(S) | : Speck et al. | |

It is certified that error appears in the above-identified patent and that said Letters Patent is hereby corrected as shown below:

ON THE TITLE PAGE:

On the Title Page, in Item (62), under "Related U.S. Application Data", in Column 1, Line 1, delete "filed" and insert -- filed on Mar. 21, 2005 --, therefor.

On the Title Page, in Item (30), under "Foreign Application Priority Data", in Column 1, Line 1, delete "102 14 847" and insert -- 102 44 847 --, therefor.

IN THE SPECIFICATION:

In Column 7, Line 38, delete "A)" and insert -- (A) --, therefor.

In Column 7, Line 40, delete "B)" and insert -- (B) --, therefor.

IN THE CLAIMS:

In Column 9, Line 11, in Claim 6, delete "lowe" and insert -- low --, therefor.

In Column 9, Line 32, in Claim 13, delete "pacitaxel" and insert -- paclitaxel --, therefor.

In Column 10, Line 7, in Claim 16, before "the", delete "matrix".

Signed and Sealed this
Ninth Day of July, 2013

Teresa Stanek Rea
*Acting Director of the United States Patent and Trademark Office*